United States Patent
Howe et al.

(10) Patent No.: US 10,966,992 B2
(45) Date of Patent: *Apr. 6, 2021

(54) VITAMIN D COMPOSITION

(71) Applicants: Bruce L. Howe, Solana Beach, CA (US); Kodimule Shyam Prasad, Bangalore (IN)

(72) Inventors: Bruce L. Howe, Solana Beach, CA (US); Kodimule Shyam Prasad, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/195,214

(22) Filed: Nov. 19, 2018

(65) Prior Publication Data

US 2019/0083514 A1    Mar. 21, 2019

Related U.S. Application Data

(63) Continuation of application No. 15/392,730, filed on Dec. 28, 2016, now Pat. No. 10,130,641.

(60) Provisional application No. 62/271,324, filed on Dec. 28, 2015.

(51) Int. Cl.

| | |
|---|---|
| *A61K 31/593* | (2006.01) |
| *A23K 20/158* | (2016.01) |
| *A23K 20/174* | (2016.01) |
| *A23L 33/155* | (2016.01) |
| *A23D 9/007* | (2006.01) |
| *A61K 9/00* | (2006.01) |
| *A61K 31/592* | (2006.01) |
| *A61K 47/44* | (2017.01) |
| *A61K 36/81* | (2006.01) |

(52) U.S. Cl.
CPC ............ *A61K 31/593* (2013.01); *A23D 9/007* (2013.01); *A23K 20/158* (2016.05); *A23K 20/174* (2016.05); *A23L 33/155* (2016.08); *A61K 9/0053* (2013.01); *A61K 9/0095* (2013.01); *A61K 31/592* (2013.01); *A61K 36/81* (2013.01); *A61K 47/44* (2013.01); *A23V 2002/00* (2013.01); *A23V 2250/194* (2013.01); *A23V 2250/2131* (2013.01); *A23V 2250/7104* (2013.01); *A23V 2250/7106* (2013.01); *A61K 2236/37* (2013.01)

(58) Field of Classification Search
None
See application file for complete search history.

(56) References Cited

U.S. PATENT DOCUMENTS 4,164,569 A * 8/1979 Ikushima
10,103,641 B2 * 10/2018 Masuzawa

OTHER PUBLICATIONS

Dr. Josh Axe, "Sardines: nutrition, benefits & recipes", draxe.com/sardines-nutrition/, document online capture date Dec. 17, 2015, downloaded on Sep. 17, 2017 from "https://web.archive.org/web/20151217192449/http://draxe.com:80/sardines-nutrition/", 17 pages.*
Nature Made, "Vitamin D3 1000 IU Liquid Softgel", naturemade.com/vitamins/vitamin-d/vitamin-d-lsg-1000-iu, document online capture date Oct. 15, 2014, downloaded on Sep. 20, 2017 from "https://web.archive.org/web/20141015202238/http://www.naturemade.com/vitamins/vitamin-d/vitamin-d-lsg-1000-iu", 1 page.*
Prema et al., "Vitamin D3 and Its Metabolites In the Tomato Plant", Phytochemistry, 1996, vol. 42(3), pp. 617-620.*
EFSA FEEDAP Panel (EFSA Panel on Additives and Products or Substances used in Animal Feed) "Scientific Opinion on the safety and efficacy of vitamin D3 (cholecalciferol) as a feed additive for all animal species or categories based on a dossier submitted by Lohmann Animal Health GmbH", EFSA Journal 2014;12(2):3568.*

* cited by examiner

*Primary Examiner* — Savitha M Rao
*Assistant Examiner* — Gregg Polansky
(74) *Attorney, Agent, or Firm* — TMB Law; Timothy M. Brown

(57) ABSTRACT

The invention is directed to compositions of vitamin D having enhanced bioavailability and enhanced stability. Methods of making and using the compositions of the invention are contemplated and disclosed.

16 Claims, 3 Drawing Sheets

VITAMIN D COMPOSITION

CROSS-REFERENCE TO RELATED APPLICATIONS

This application is a continuation of U.S. application Ser. No. 15/392,730 filed Dec. 28, 2016, now U.S. Pat. No. 10,130,641, which claims priority to U.S. Provisional Application No. 62/271,324, filed Dec. 28, 2015. The entire contents of the aforementioned applications are incorporated herein by reference for all purposes.

FIELD OF THE INVENTION

The invention generally relates to nutraceuticals. More particularly, the invention relates to compositions of vitamin D formulated to achieve enhanced stability and enhanced bioavailability.

RELATED ART

Vitamin D is an oil-soluble micronutrient that is essential in the human diet for maintaining good health. It has two major chemical forms: vitamin D2 (ergocalciferol) and vitamin D3 (cholecalciferol). Vitamin D3 has more potency than vitamin D2 in humans and it is usually synthesized in the skin after exposure to light. Vitamin D3 may exist in a number of different chemical forms depending on environmental conditions (e.g. calciol, calcidiol, and calcitriol). Calcitriol (25-dihydroxyvitamin D3) is the biologically active form of vitamin D3 and controls calcium and phosphorus homeostasis, intestinal transport, bone metabolism, renal calcium reabsorption, blood pressure, and insulin secretion.

Vitamin D3 deficiency often occurs in people who are not exposed to sufficient sunlight, and in individuals with metabolic disorders (e.g. obesity or hyperparathyroidism) gastrointestinal disorders (e.g. celiac, cystic fibrosis or inflammatory bowel disease) and kidney dysfunction. Vitamin D deficiency can lead to malfunction in the regulation of calcium and phosphorus absorption which can result in defects in bone metabolism, osteoporosis and osteomalacia (pore formation and softening of bones). Vitamin D deficiency in children can result in rickets which is often observed in children in developing countries. While Vitamin D is fairly limited in foods, available sources include products such as beef liver, dairy products, egg yolk, and fish.

Confounding the problem of vitamin D's limited availability in foods is the fact that vitamin D3 is highly sensitive to environmental stresses such as light, heat, and oxygen. These stresses can oxidize Vitamin D3 and destroy its function and physiological benefits. All forms of vitamin D, including activated ergosterol, activated 7-dehydrocholesterol (crystalline vitamin D3), as well as vitamin D from natural sources, are susceptible to such degradation. Various methods for stabilizing vitamin D have been tested. Such methods include the use of coating agents such as dried whey, packing in inert gases, and the addition of stabilizing substances such as yeast, alfalfa meal and $CaCO_3$. Deterioration of vitamin D3 preparations is negligible after 12 months of storage at low temperatures. However, storage of vitamin D3 preparations in amber evacuated containers at higher refrigerated temperatures (>23° C.) show inferior stability upon exposure to light of various intensities.

In view of the limited availability and instability of vitamin, there is a need for providing vitamin D3 with improved stability and improved bioavailability.

BRIEF SUMMARY OF THE INVENTION

The inventors discovered that the degradation of vitamin D, due to environmental factors such as exposure to light, heat, moisture and oxygen can be inhibited by formulating vitamin D with selected comestible oils. In addition to inhibiting the degradation of vitamin D, the comestible oils of the invention increase the bioavailability of vitamin D. The inventors further discovered that vitamin D for practicing the present invention can be purified from tomato leaf using supercritical extraction. The inventors have tested this source of vitamin D using different experimental approaches to prove its effectiveness in the present formulation in enhancing vitamin D stability and bioavailability.

DEFINITIONS

Figure 1:
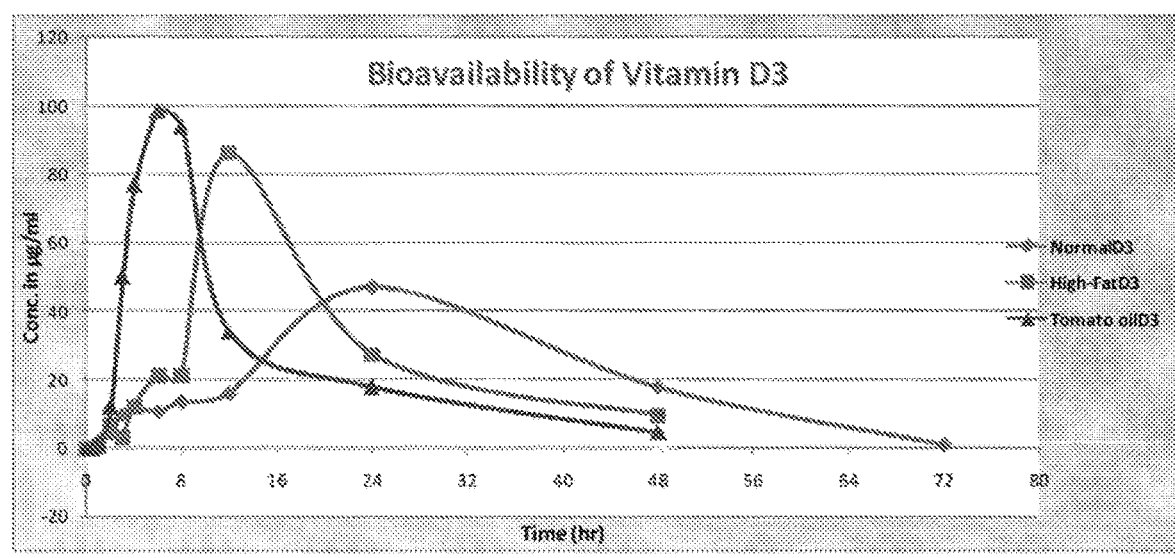
FIG. 1 shows bioavailability of vitamin D3 in rats (concentration in μg/ml).
Figure 2A:
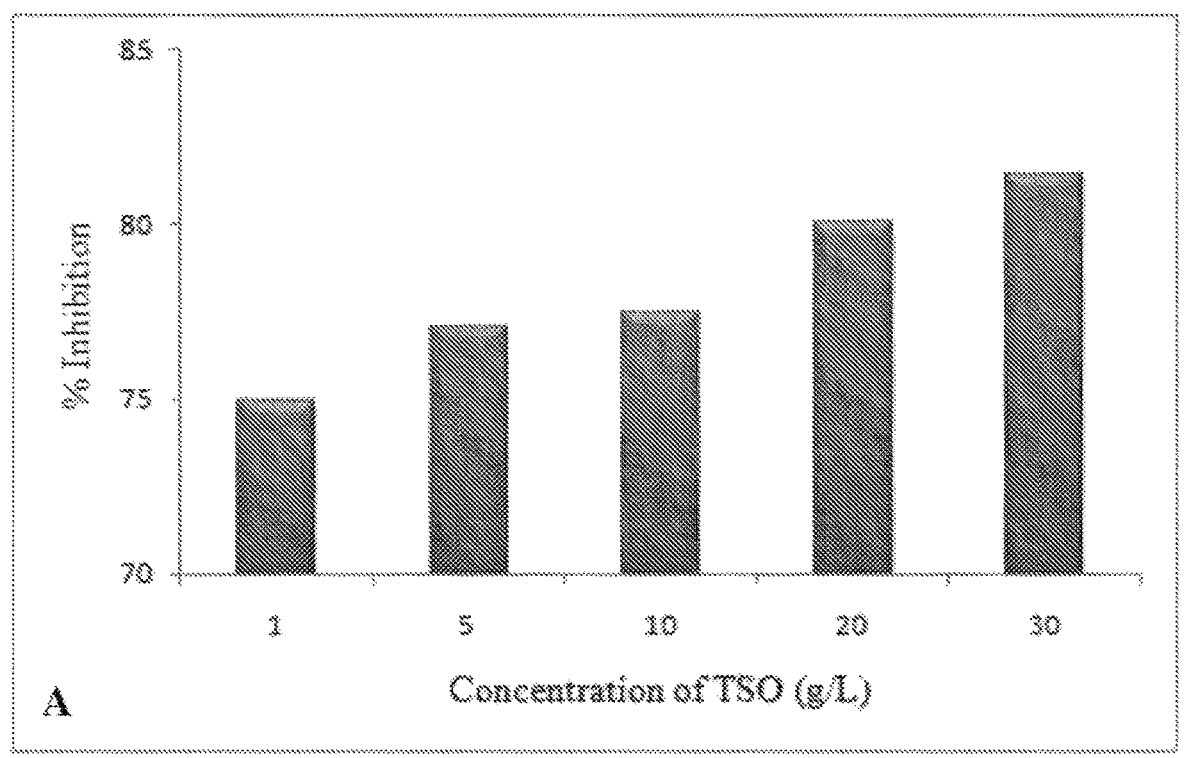
FIG. 2A shows the evaluation of antioxidant capacities of tomato seed oil in DPPH assay.
Figure 2B:
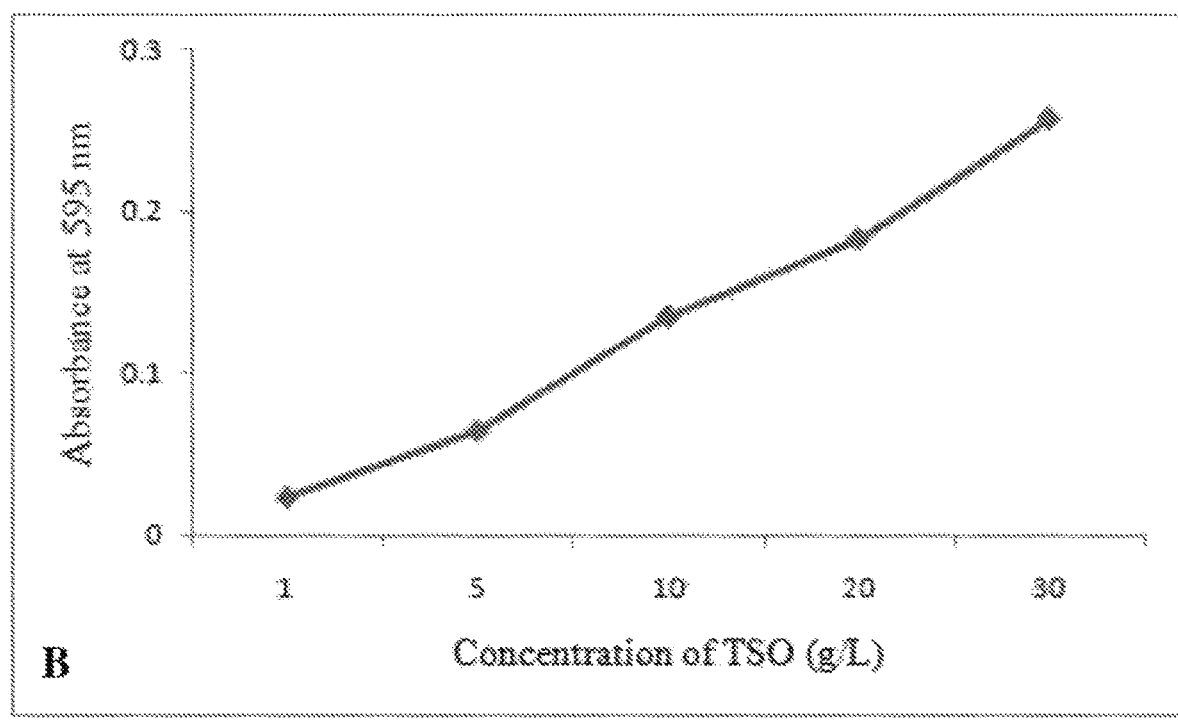
FIG. 2B shows the evaluation of antioxidant capacities of tomato seed oil in FRAP assay.
Figure 3:
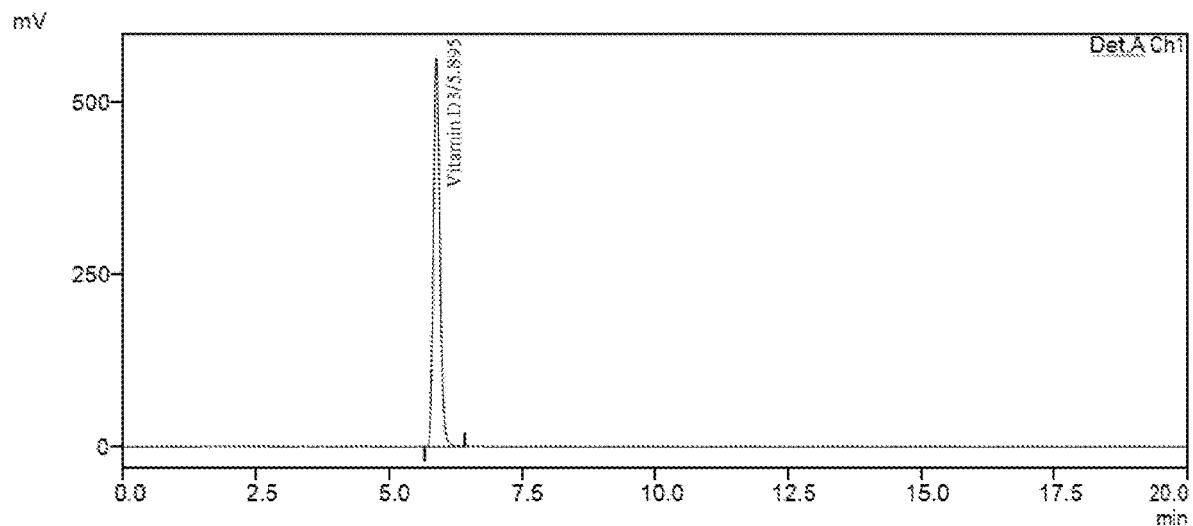
FIG. 3 shows HPLC chromatogram of vitamin D3 standard.
Figure 4:
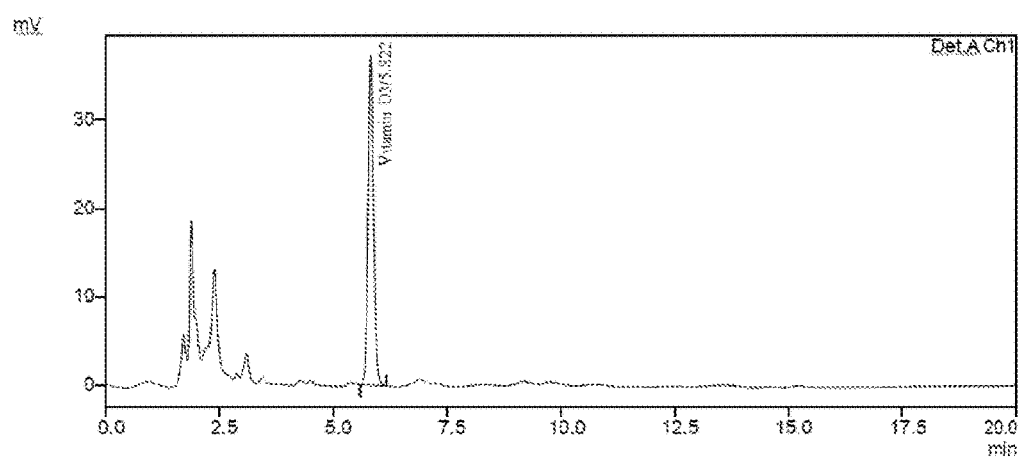
FIG. 4 shows HPLC chromatogram of vitamin D3 from tomato leaf.

The phrase "vitamin D," as used herein, refers to all vitamin D species, including vitamin D2 and vitamin D3. "Vitamin D2," as used herein, refers to vitamin D2 in all its forms, including ergocalciferol, ergosterol, and 7-dehydrocholesterol. "Vitamin D3," as used herein, refers to vitamin D3 in all its forms, including cholecalciferol, calciol, calcidiol, and calcitriol (25-dihydroxyvitamin D3).

The term "purified," as used herein, refers to a substance that, prior to combining (e.g. contacting) with another substance, is at least 75%, 85%, 90%, 95%, 100% free of any other sub stance.

The term "subject," as used herein, typically refers to a human. In certain embodiments, a subject is a non-human mammal. Exemplary non-human mammals include, but are not limited to, laboratory, domestic, pet, sport, and stock animals, e.g., mice, rats, cats, dogs, horses, sheep, and bovids (e.g. cows). Subjects can once have been used as controls.

The term "bioavailability" as used herein refers to the proportion of a drug or other substance (e.g. vitamin D) that enters the circulation when introduced into the body and so is able to have an active effect.

The phrases "enhanced stability" and "increased stability," when used in reference to vitamin D, refer to the ability of a set of conditions to inhibit the degradation of vitamin D compared to the degradation of vitamin D under control conditions.

DETAILED DESCRIPTION

The invention relates to compositions of vitamin D and methods for their use and manufacture. More particularly, the invention provides compositions of vitamin D formulated to achieve enhanced stability and enhanced bioavailability and methods of making and using such compositions.

Vitamin D is degraded by environmental factors such as light, oxygen, moisture and temperature. These factors can have a significant effect on efforts to supplement the diet with vitamin D as vitamin D supplements may be completely or partially degraded before they can be consumed. The inventors discovered that the stability of vitamin D can be enhanced by combining it with selected comestible oils which inhibit its degradation. In addition, the compositions of the invention provide enhanced vitamin D bioavailability. Thus, the invention greatly increases the ability to supplement the diet with vitamin D by providing compositions that contain greater amounts of active vitamin D despite having been stored over time, while simultaneously increasing the vitamin D's ability to be absorbed by the body.

In some aspects, the invention provides a method of making a composition of vitamin D, wherein the method comprises contacting vitamin D with at least one comestible oil, wherein contacting the vitamin D with the comestible oil enhances the stability of the vitamin D compared to control vitamin D that has not been contacted with the comestible oil.

In some aspects, the invention provides a method of making a composition of vitamin D, wherein the method comprises contacting vitamin D with at least one comestible oil, wherein contacting the vitamin D with the comestible oil enhances the bioavailability of the vitamin D compared to control vitamin D that has not been contacted with the comestible oil.

In some aspects, the invention provides a method of making a composition of vitamin D, wherein the method comprises contacting vitamin D with at least one comestible oil, wherein contacting the vitamin D with the comestible oil enhances the stability and bioavailability of the vitamin D compared to control vitamin D that has not been contacted with the comestible oil.

In some aspects, the invention provides a composition of vitamin D, wherein the composition comprises vitamin D in contact with at least one comestible oil capable of enhancing the stability of the vitamin D.

In some aspects, the invention provides a composition of vitamin D, wherein the composition comprises vitamin D in contact with at least one comestible oil capable of enhancing the bioavailability of the vitamin D.

In some aspects, the invention provides a composition of vitamin D, wherein the composition comprises vitamin D in contact with at least comestible oil capable of enhancing the stability and bioavailability of the vitamin D.

Vitamin D for use with the invention can be purified vitamin D, or a composition that comprises vitamin D. For example, the vitamin D can be a mixture that contains vitamin D. The vitamin D can be contained in a food, food supplement, or nutritional supplement that is contacted with at least one comestible oil capable of enhancing the stability and/or bioavailability of the vitamin D. The vitamin D can be obtained from natural sources or synthetic sources. The vitamin D can be contained in an extract obtained from plant material, such as tomato leaf, for example. The vitamin D can be vitamin D2, vitamin D3, or a combination thereof. The vitamin D2 can be ergocalciferol, ergosterol, 7-dehydrocholesterol, or a combination thereof. The ergocalciferol, ergosterol, and/or 7-dehydrocholesterol can be purified. The vitamin D3 can be cholecalciferol, calciol, calcidiol, calcitriol (25-dihydroxyvitamin D3), or a combination thereof. The cholecalciferol, calciol, calcidiol, and/or calcitriol (25-dihydroxyvitamin D3) can be purified. In a specific, non-limiting embodiment, the composition comprises purified calcitriol and at least one comestible oil. The vitamin D can be selected from the group consisting of ergocalciferol, ergosterol, 7-dehydrocholesterol, cholecalciferol, calciol, calcidiol, calcitriol (25-dihydroxyvitamin D3), and a combination thereof.

Comestible oils for use with the invention can be any comestible oil capable of increasing at least one of the bioavailability and stability of vitamin D. The comestible oil can be tomato seed oil, corn oil, olive oil, canola oil, palm oil, safflower oil, sunflower oil, sesame oil, peanut oil, coconut oil, rapeseed oil, grape seed oil, soybean oil, cottonseed oil, or a combination thereof. The comestible oil can be selected from the group consisting of tomato seed oil, corn oil, olive oil, canola oil, palm oil, safflower oil, sunflower oil, sesame oil, peanut oil, coconut oil, rapeseed oil, grape seed oil, soybean oil, cottonseed oil, and a combination thereof. The comestible oil can be tomato seed oil. The composition can comprise vitamin D in contact with tomato seed oil. The composition can comprise vitamin D2 and vitamin D3 in contact with tomato seed oil. The composition can comprise vitamin D3 in contact with tomato seed oil. The composition can comprise calcitriol in contact with tomato seed oil. The comestible oil can be purified.

Vitamin D for use with the invention may be obtained from any source that provides vitamin D having nutritive value in a subject. Vitamin D can be purified vitamin D. In one non-limiting embodiment, vitamin D is obtained from plant material. Vitamin D can be obtained from tomato leaf, for example. Such vitamin D can be vitamin D2 and/or vitamin D3. Vitamin D3 obtained from tomato leaf can be calciol, calcidiol, calcitriol (e.g. 25-dihydroxyvitamin D3) or a combination thereof. In one non-limiting embodiment, the vitamin D3 obtained from tomato leaf is calcitriol. Tomato leaf for providing vitamin D for use with the invention can be dried tomato leaf, fresh tomato leaf, or a combination thereof.

In some aspects of the invention, the vitamin D and comestible oil are present in specific amounts. The compositions of the invention can be practiced with 1%, 5%, 10%, 15%, 20%, 25%, 30%, 40%, or 50% vitamin D, with the remainder of the composition being the at least one comestible oil. The vitamin D can be present in an amount intervening these specifically listed amounts. The invention further contemplates methods of making such compositions, wherein vitamin D is contacted with the at least one comestible oil in accordance with the presently disclosed amounts.

Vitamin D can be obtained from plant material using any method capable of extracting vitamin D from the plant material. Such methods include, for example, extraction using polar or non-polar solvents. The vitamin D can be obtained from plant materials by ethanol extraction, aqueous extraction, or by supercritical fluid extraction. As used herein, "supercritical fluid extraction" or "SFE" refers to the process of separating one or more components (extractant) from another (matrix) using supercritical fluids as the extracting solvent. Supercritical fluids for extracting vitamin D include, but are not limited to, carbon dioxide, water, methane, ethane, propane, ethylene, propylene, methanol, ethanol, acetone, and nitrous oxide. In a preferred, non-limiting embodiment, the supercritical fluid is carbon dioxide. Vitamin D can be obtained from a plant material (e.g. tomato leaf) by extrusion.

The compositions disclosed herein can be formulated for administration to a subject. Accordingly, the compositions can be formulated with a pharmaceutically acceptable carrier. Suitable carriers for combining with the compositions disclosed herein are described in Remington's Pharmaceutical Sciences, 19th Edition, Mack Publishing Co., Easton, Pa. 1995, the entire contents of which are incorporated herein by reference in their entirety for all purposes. The pharmaceutical carrier can be an artificial pharmaceutical carrier. The concentration of the composition when combined with the carrier can range from 10 µg/mL to about 1,000 µg/mL, including all intervening concentrations at about 1 µg/mL increments.

The compositions can be formulated as powders, pills, tablets, pellets, capsules, thin films, solutions, sprays, syrups, linctuses, lozenges, pastilles, chewing gums, pastes, vaporizers, suspensions, emulsions, ointments, creams, lotions, liniments, gels, drops, topical patches (e.g. adhesive topical patches or transdermal patches), buccal patches, beads, gummies, gels, sols, injections and the like. The compositions of the invention can comprise an extract that is dried to form one or more of the foregoing dosage administration forms.

The compositions of the invention can be combined with ordinary foods to enhance the vitamin D content of the foods. For example, the compositions can be mixed with drinks, food supplements, nutritional supplements, snacks, bars, and virtually any other food, nutritional product or drink that is desired to be supplemented with vitamin D. Thus, the invention specifically includes food substances of specific types combined with the compositions of the invention in specified forms and quantities. The compositions of the invention may be combined with one or more substances to increase the nutritive value of the composition, such substances including, but not limited to, vitamins, minerals, amino acids, proteins, and combinations thereof.

In some aspects, the invention provides a method for providing vitamin D to a subject. The compositions disclosed herein can be administered to a subject in an amount effective to supplement vitamin D levels in the subject. The compositions can be administered to a subject by various routes including but not limiting to topically, orally, buccally, intraaeterially, intravenously, intraperitoneally, sublingually, rectally, by inhalation, or a combination thereof. The composition can be administered to the subject one or more times. The composition can be administered to the subject one or more times per day. The subject can be a subject that has, or is at risk of developing, a vitamin D deficiency. The subject can have, or be at risk of developing, the symptoms of vitamin D deficiency. The composition can be administered to a subject to prevent or relieve the symptoms of vitamin D deficiency. The subject can have, or be at risk of developing, a malfunction in the regulation of calcium and phosphorus absorption, kidney dysfunction, a defect in bone metabolism, osteoporosis, osteomalacia, or rickets.

Vitamin D is subject to degradation due to exposure to light, heat, oxygen and moisture. Thus, in some aspects, methods of enhancing the stability of vitamin D are provided. In such methods, vitamin D is contacted with at least one comestible oil capable of enhancing the stability of the vitamin D. As used herein, the term "enhance" when used in reference to the stability of vitamin D, refers to any measurable inhibition in the degradation of vitamin D that results from a given set of conditions compared to a control set of conditions. As the invention relates to enhancing the stability of vitamin D, the invention can be used to increase the shelf life of vitamin D. Thus, the invention provides a method of extending the shelf life of vitamin D comprising placing the compositions disclosed herein in a container, and storing the container under suitable conditions. The compositions can be frozen, refrigerated or freeze-dried prior to or after being placed in the container. The container can be stored in the absence of light, and/or in the absence of oxygen (e.g. under vacuum). The container can be vacuum sealed. The container can be constructed of glass or suitable plastic (e.g. PET, vinyl, polyethylene). The container can be darkened to prevent the penetration of light. The container can be a bottle, vial, ampule, sachet, stick pack, or foil pack.

Example 1—Tomato Seed Oil Increases Vitamin D3 Absorption

The present study was undertaken to compare the rate of absorption of vitamin D3, from formulated vitamin D3 with tomato seed oil and high-fat meal. The absorption was studied by serial measurements of the plasma concentration of vitamin D3 after ingestion of a pharmacological dose of the vitamin dissolved in the vehicles.

TABLE 1

| Experimental Groups | |
|---|---|
| Animals | Wistar Rats |
| Body weight | 300-350 g |
| Total number of animals | 15 |
| Sex | Male |
| Housing | 3/cage, male and male in separate cages, 12 hrs |
| Temperature | 25 ± 2° c. |

TABLE 2

| Treatment Conditions | | |
|---|---|---|
| Groups | Treatment | Sample |
| I | Vitamin D3 50,000 IU + Normal diet | 5 |
| II | Vitamin D3 50,000 IU + High-Fat diet. | 5 |
| III | Vitamin D3 50,000 IU with tomato oil | 5 |

TABLE 3

| Composition of High-Fat Diet: Atherogenic diet | |
|---|---|
| Cholesterol | 1% w/w |
| Cholic acid | 0.5% w/w |
| Lard oil | 5% w/w |

1.1 Drug Administration and Blood Sampling

Male Albino Wistar rats were used Animals were kept under a twelve-hour light/dark cycle. Group I was treated with normal diet and vitamin D3 (50,000 IU). Group II was given Vitamin D3 (50,000 IU) with High-Fat diet. Group III was treated with Vitamin D3 (50,000 IU) formulation in tomato seed oil orally. 10 mL/kg body weight was used for gavage administration. Blood was collected at time 0 (pre-dose), 30 min and 1, 2, 3, 4, 6, 8, 12, and 24 h after dose administration. Animals were ether anesthetized and blood samples (approximately 0.5 mL) were collected via retro-orbital sinus puncture.

1.2 Extraction from Plasma and Analytical Procedure

Blood samples were collected in heparinized eppendorf tubes. Tubes were inverted several times to mix and were then placed on ice and centrifuged to separate plasma within 1 h time. After centrifugation, plasma was transferred into storage tubes (0.5 mL), which were stored frozen (approximately −70° C.) until analyzed.

Plasma processing involved liquid-liquid extraction using acetonitrile and methanol (80:20). 100 µL aliquot of plasma was mixed with 1 mL of acetonitrile and methanol. After vortex mixing for 1 min, the sample was centrifuged at 7,000 rpm at 4° C. for 10 min to remove precipiSUBtated proteins; the supernatant was transferred to a clean tube and dried under nitrogen at room temperature (approximately 25° C.). After the evaporation was completed, the residue was reconstituted in 100 μL of methanol with 5 min of sonication, added to 400 μL of water, vortex mixed, and centrifuged again. The resulting supernatant was transferred to a sample vial for instrumental analysis.

Chromatography was performed using a Phenomenex C18 150 cm×4.6 mm, 5 μm column, maintained at a temperature of 35° C. A flow rate of 1 mL/min was used; mobile phase acetonitrile and methanol (80:20); elution gradient program, injection volume 5 detection UV, 280 nm. Total run time was 15 min.

1.3 Pharmacokinetic Determination

The data was represented in a plasma level-time curve. The area under time curve (AUC) was calculated using Trapezoid rule. The maximum concentration ($C_{max}$) and maximum time ($T_{max}$) were obtained directly from generated data. The maximum plasma concentration ($C_{max}$) and the time to reach $C_{max}$ ($T_{max}$) were obtained directly from the plasma concentration-time curve. All values were expressed as mean±standard deviation (SD) except $T_{max}$ mentioned as median.

1.4 Results

The efficiency of the tomato seed oil in enhancing the bioavailability of D3 was evaluated in vivo by comparing with high-fat diet (force feeding) in rats. The mean plasma concentrations of vitamin D3 after single oral administration (50,000 IU) are shown in Table 1. The peak concentration occurred at 6 to 24 hours. Group III (administered with D3 formulation in tomato seed oil) showed higher peak plasma concentration than Group I and Group II. The mean plasma concentration was 98.81+0.54 at $T_{max}$ of 6 h when Vitamin D3 administered in tomato seed oil (Group III).

The high-fat diet (Group II) and normal diet (Group I) mean plasma concentrations were 86.09+12.14 at $T_{max}$ of 12 hr and 47.03+4.15 at $T_{max}$ of 24 h respectively. There was a statistically significant difference in peak concentration and area under curve (AUC) between the groups.

TABLE 4

Pharmacokinetic parameters derived from rat plasma

| | Tmax | Cmax | |
|---|---|---|---|
| Vitamin D3 + Normal Diet (Conc. in μg/ml) | 24 hr | 47.03 + 4.15 | 3478 + 1758 μg · hr/ml |
| Vitamin D3 + High-Fat Diet (Conc. in μg/ml)) | 12 hr | 86.09 + 12.14 | 1595 + 600.6 μg · hr/ml |
| Vitamin D3 + Tomato seed oil (Conc. in μg/ml)) | 6 hr | 98.81 + 0.54 | 1358 + 54.17 6 μg · hr/ml |

*$C_{max}$: Maximum conc.; and $T_{max}$: Time to reach $C_{max}$;
AUC: Area Under the plasma conc.-time Curve.
Data expressed as mean ± SE except Tmax mentioned as mean.

We have carried out stability study of our D3 formulation and in vitro antioxidant activities of tomato seed oil. The study demonstrates that oxidative destruction of vitamin D3 is minimized in the presence of tomato seed oil and it is comparatively superior to other comestible oils in preventing the deterioration of D3.

Example 2—Comparative Stability Studies of Vitamin D3 Formulations in Comestible Oils The formulation of D3 in tomato seed oil from Example 1 was examined for stability and compared with solutions of vitamin D3 in corn oil and olive oil. All the samples were sealed in clear PET bottles, irradiated and kept at 23° C. for 3 months. The samples were subjected to photo oxidation at 23° C. and evaluated for D3 destruction at regular intervals using HPLC (HPLC-LC 2010 CHT).

2.1. Analysis

Instrument used for the analysis was HPLC-LC 2010 CHT, with UV-Vis detection, at 280 nm & column C-18, 5 μm, 150×4.6 mm Phenomenex (Kinetex), Mobile phase was A: Acetonitrile; B: methanol (80:20) with flow rate 1.0 ml/min. Acquisition is stopped at dissolving approximately 5-20 min. Vitamin D3 standard 97% mg of standard 97% Vitamin D3 in was prepared by 50 mL of diluent (Acetonitrile and methanol 80:20). The test sample vitamin D3 from tomato leaf was prepared by dissolving approximately 200 mg of extract in 50 mL of same diluent. Both the standard and sample were filtered using Whatmann filter paper No. 41 and transferred to the HPLC vials. 3 μl was injected in autosampler.

2.2. Results

In view of the reports in the literature, it has seemed desirable to report stability data on our novel formulation of D3 kept under the most severe conditions of storage likely to be encountered in practice. The study indicated deterioration occurred in all the solutions; however, interestingly the formulation with tomato seed oil resulted in negligible D3 losses due to photo oxidation. This indicates a protective action of seed oil against oxidative destruction of D3.

TABLE 5

Stability of vitamin D3 formulation in various comestible oils

| | Vitamin D3 (IU) | | | |
|---|---|---|---|---|
| Carrier | Original | 1 month | 2 months | 3 months |
| Tomato seed oil | 40000 | 36400 | 34400 | 28800 |
| Corn oil | 40000 | 23200 | 17200 | 9200 |
| Olive oil | 40000 | 29200 | 28800 | 22800 |

Appropriate dilutions of samples were made before the study

Example 3—Antioxidant Capacity of Tomato Seed Oil in Solution

A number of observations indicate that the presence of fat which becomes rancid during storage period accelerates destruction of Vitamin D. It seems apparent that the development of rancidity in the oil presents a detrimental effect upon vitamin D3. Tomato seed oil contains 20% of saturated fat making it less susceptible to rancidity, and hence the vitamin D3 remained stable.

Tomato seed oil is generally recognized as containing natural antioxidants. These include the non-glyceride fraction of the oil. A partial protection of vitamin D3 is due to the antioxidant capacity of oil. In vitro study data relative to the antioxidant activity of tomato seed oil are as follows.

3.1. DPPH Free Radical Scavenging Assay

To determine the capacity of tomato seed oil (TSO) to scavenge the chromogenic free nitrogen DPPH radical, 0.5 ml freshly prepared 0.3 mM DPPH solution in ethanol was mixed with TSO solution (1.0 ml in n-hexane). The mixture was shaken on a thermal shaker (15 min, 25±1° C., 1000 rpm). Afterwards, the absorbance of the mixture was detected at 540 nm using a spectrophotometer (Muller et al. 2011).

3.2. Ferric Ion Reducing Antioxidant Power (FRAP) Assay

FRAP of TSO was analyzed by mixing TSO (100 µL, dissolved in n-hexane) with 1.0 mL of FRAP reagent on a thermal shaker (6 min, 25±following the FRAP procedure used for oil samples by 1° C., 1400 rpm) Müller et al (2011). FRAP reagent contained 300 Mm acetate buffer pH 3.6, 10 mM TPTZ (Sigma-Aldrich, India) in 40 mM hydrochloric acid and 20 mM aqueous $FeCl_3$ solution. After shaking the solution was transferred completely into half-microcuvettes (1.5 mL, polystyrene) and centrifuged for 30 s at 1000 g. Exactly 8 min after starting shaking, the absorbance at 595 nm of the aqueous layer was detected in a spectrophotometer.

3.3. Results

In both the assays tested, TSO exhibited potent antioxidant activity. In DPPH assay, TSO bleached the DPPH solution very strongly with the increasing concentrations (FIG. 1A). The IC50 value recorded was 14.6 g/L. Such a strong antioxidant effect was also seen in FRAP assay (FIG. 1B). Our results are in accordance with the previous findings. Muller et al. (2013) reported that TSO was able to counteract spontaneous and $H_2O_2$ induced oxidative stress in human macrophages controlling oxidative stress signaling.

Example 4—Extraction of Vitamin D3

Take 100 kg of powdered fresh tomato leaves into a clean 200 L super critical extractor. Raise the temperature to 60° C. and pressure to 300 bar slowly about ½ an hour to 1 hour and maintain temperature 60-65° C. and pressure 300-325 bar about 4-5 hours. Release the temperature and pressure slowly; collect the extract in a receiver tank with a yield about 0.5±0.10%. Take the extract into a clean 50 L reactor, add about 10 L of 90 v/v % ethanol under stirring, stir about ½ an hour and kept for settling. Collect the upper organic layer. Repeat the aqueous 90 v/v % ethanol wash two more times and collect the entire organic layer and concentrate to dryness.

4.1. HPLC Analysis

Instrument used for the analysis was HPLC-LC 2010 CHT, with UV-Vis detection, at 280 nm & column C-18, 5 µm, 150×4.6 mm Phenomenex (Kinetex), Mobile phase was A: Acetonitrile; B: methanol (80:20) with flow rate 1.0 ml/min. Acquisition is stopped at 20 min. Vitamin D3 standard 97% was prepared by dissolving approximately 5 mg of standard 97% Vitamin D3 in 50 mL of diluent (Acetonitrile and methanol 80:20). The test sample vitamin D3 from tomato leaf was prepared by dissolving approximately 200 mg of extract in 50 mL of same diluent. Both the standard and sample were filtered using Whatmann filter paper No. 41 and transferred to the HPLC vials. 3 µl was injected in an autosampler.

REFERENCES

1. Muller L, Frohlich K, Bohm V. Comparative antioxidant activities of carotenoids measured by ferric reducing antioxidant power (FRAP), ABTS bleaching assay (aTEAC), DPPH assay and peroxyl radical scavenging assay. *Food Chem* 2011; 129:139-148.
2. Müller L, Goupy P, Frö hlich K, Dangles O, Caris-Veyrat C, Bö hm V. Comparative study on antioxidant activity of lycopene (Z)-isomers in different assays. *J Agric Food Chem* 2011; 59: 4504-4511.
3. Müller L, Catalano A, Simone R, Cittadini A, Frö hlich K, Bö hm V. Palozza P. Antioxidant capacity of tomato seed oil in solution and its redox properties in cultured macrophages. *J Agric Food Chem* 2013; 61: 346-354.

The invention claimed is:

1. A vitamin D composition comprising vitamin D in contact with tomato seed oil, wherein said contact increases the bioavailability and stability of said vitamin D compared to control vitamin D that has not been contacted with said tomato seed oil.

2. The composition of claim 1, wherein said vitamin D is selected from the group consisting of vitamin D2, vitamin D3, and a combination thereof.

3. The composition of claim 1, wherein said vitamin D retains at least 90 percent of its activity 30 days after it is contacted with said tomato seed oil.

4. The composition of claim 1, wherein said vitamin D retains at least 86 percent of its activity 60 days after it is contacted with said tomato seed oil.

5. The composition of claim 1, wherein said vitamin D retains at least 72 percent of its activity 90 days after it is contacted with said tomato seed oil.

6. The composition of claim 1, wherein said contact increases the bioavailability of said vitamin D by about 2 fold.

7. The composition of claim 1, wherein at least one of said vitamin D and said tomato seed oil are purified.

8. The composition of claim 1, wherein said vitamin D is tomato leaf vitamin D.

9. The composition of claim 1, wherein said composition further comprises a pharmaceutical carrier.

10. The composition of claim 1, wherein said composition is in a form selected from the group consisting of a powder, pill, tablet, pellet, capsule, thin film, solution, spray, syrup, linctus, lozenge, chewing gum, paste, vaporizer, suspension, emulsion, ointment, cream, lotion, liniment, gel, drop, topical patch, buccal patch, bead, gummy, gel, sol, and injection.

11. The composition of claim 1, wherein said composition is in contact with a food, food supplement, nutritional supplement, or beverage.

12. The composition of claim 1, wherein said composition is enclosed within a container.

13. A vitamin D composition, comprising a mixture of vitamin D and tomato seed oil, wherein said vitamin D has enhanced bioavailability and stability compared to vitamin D that is not in a mixture with said tomato seed oil.

14. The vitamin D composition of claim 13, wherein at least one of said vitamin D and said tomato seed oil are purified.

15. The vitamin D composition of claim 13, wherein said composition further comprises a pharmaceutical carrier.

16. The vitamin D composition of claim 13, wherein said composition is in a form selected from the group consisting of a powder, pill, tablet, pellet, capsule, thin film, solution, spray, syrup, linctus, lozenge, chewing gum, paste, vaporizer, suspension, emulsion, ointment, cream, lotion, liniment, gel, drop, topical patch, buccal patch, bead, gummy, gel, sol, and injection.

* * * * *